(12) United States Patent
Potter et al.

(10) Patent No.: US 11,944,743 B2
(45) Date of Patent: Apr. 2, 2024

(54) VAPOR PROVISION SYSTEMS

(71) Applicant: NICOVENTURES TRADING LIMITED, London (GB)

(72) Inventors: Mark Potter, London (GB); Ugurhan Yilmaz, London (GB)

(73) Assignee: NICOVENTURES TRADING LIMITED, London (GB)

( * ) Notice: Subject to any disclaimer, the term of this patent is extended or adjusted under 35 U.S.C. 154(b) by 518 days.

(21) Appl. No.: 16/762,288

(22) PCT Filed: Nov. 2, 2018

(86) PCT No.: PCT/GB2018/053187
§ 371 (c)(1),
(2) Date: May 7, 2020

(87) PCT Pub. No.: WO2019/092405
PCT Pub. Date: May 16, 2019

(65) Prior Publication Data
US 2020/0282156 A1 Sep. 10, 2020

(30) Foreign Application Priority Data
Nov. 8, 2017 (GB) ...................................... 1718462

(51) Int. Cl.
*G08B 21/04* (2006.01)
*A61M 11/04* (2006.01)
(Continued)

(52) U.S. Cl.
CPC .......... *A61M 11/042* (2014.02); *A61M 15/06* (2013.01); *A61M 16/0003* (2014.02);
(Continued)

(58) Field of Classification Search
USPC ... 340/539.12, 539.24, 539.3, 636.1, 636.19, 340/680, 3.1, 825.24
See application file for complete search history.

(56) References Cited

U.S. PATENT DOCUMENTS 6,626,133 B2 * 9/2003 Schell ................... F24H 9/2035
122/504
8,495,998 B2 7/2013 Schennum
(Continued)

FOREIGN PATENT DOCUMENTS

CA 2982164 A1 10/2016
CN 103948177 A 7/2014
(Continued)

OTHER PUBLICATIONS

International Search Report and Written Opinion, Application No. PCT/GB2018/053187, dated Jan. 30, 2019, 12 pages.
(Continued)

*Primary Examiner* — Daniel Previl
(74) *Attorney, Agent, or Firm* — Husch Blackwell LLP

(57) ABSTRACT

A vapor provision system includes an inhalation sensor; an input button; control circuitry and a vaporizer for generating vapor from a vapor precursor material when provided with power from the control circuitry, wherein the control circuitry is configured to provide power for the vaporizer to generate vapor both in response to determining from signaling received from the inhalation sensor that a user is inhaling on the vapor provision system and in response to determining from signaling received from the input button that a user has activated the input button for at least a threshold amount of time.

13 Claims, 2 Drawing Sheets

(51) Int. Cl.
*A61M 15/06* (2006.01)
*A61M 16/00* (2006.01)

(52) U.S. Cl.
CPC .............. *A61M 2016/0015* (2013.01); *A61M 2016/0027* (2013.01); *A61M 2016/003* (2013.01); *A61M 2205/3379* (2013.01); *A61M 2205/8206* (2013.01)

(56) References Cited

U.S. PATENT DOCUMENTS

| | | | |
|---|---|---|---|
| 8,689,786 | B2 | 4/2014 | Schennum |
| 8,950,395 | B2 | 2/2015 | Schennum |
| 11,298,479 | B2 | 4/2022 | Fraser |
| 2008/0092912 | A1 | 4/2008 | Robinson et al. |
| 2011/0226236 | A1 | 9/2011 | Buchberger |
| 2011/0238010 | A1 | 9/2011 | Kirschenman et al. |
| 2012/0174914 | A1 | 7/2012 | Pirshafiey et al. |
| 2012/0260926 | A1 | 10/2012 | Tu et al. |
| 2013/0087160 | A1 | 4/2013 | Alexandru |
| 2013/0220315 | A1* | 8/2013 | Conley ............... A24F 40/44 128/202.21 |
| 2013/0255702 | A1 | 10/2013 | Griffith |
| 2014/0096781 | A1 | 4/2014 | Sears et al. |
| 2014/0338685 | A1 | 11/2014 | Amir |
| 2016/0213065 | A1 | 7/2016 | Wensley et al. |
| 2016/0227840 | A1* | 8/2016 | Xiang .................... A24F 40/51 |
| 2016/0309787 | A1 | 10/2016 | Hawes |
| 2016/0316821 | A1* | 11/2016 | Liu ....................... A61M 15/06 |
| 2016/0331035 | A1 | 11/2016 | Cameron |
| 2017/0079329 | A1 | 3/2017 | Zitzke |
| 2017/0121911 | A1 | 5/2017 | Anand et al. |
| 2017/0135412 | A1 | 5/2017 | Cameron |
| 2017/0150756 | A1 | 6/2017 | Rexroad |
| 2017/0181471 | A1 | 6/2017 | Phillips |
| 2017/0222468 | A1 | 8/2017 | Schennum et al. |
| 2017/0238606 | A1 | 8/2017 | Matsumoto et al. |
| 2018/0093054 | A1* | 4/2018 | Bowen ................. A61M 15/06 |
| 2018/0184711 | A1* | 7/2018 | Dickens ................ A24F 40/40 |
| 2021/0345681 | A1* | 11/2021 | Cameron .............. A24F 40/53 |

FOREIGN PATENT DOCUMENTS

| | | |
|---|---|---|
| CN | 205358229 | 7/2016 |
| EP | 1618803 A1 | 1/2006 |
| EP | 2110034 A1 | 10/2009 |
| EP | 2878214 A1 | 6/2015 |
| GB | 2507103 A | 4/2014 |
| JP | H02124082 A | 5/1990 |
| JP | 2014512207 A | 5/2014 |
| JP | 2014524313 A | 9/2014 |
| JP | 2017523785 A | 8/2017 |
| KR | 20110132290 A | 12/2011 |
| KR | 101162688 B1 | 7/2012 |
| KR | 101233985 B1 | 2/2013 |
| KR | 101285219 B1 | 7/2013 |
| KR | 20160012852 A | 2/2016 |
| KR | 20160044712 | 4/2016 |
| KR | 20170030558 A | 3/2017 |
| RU | 122000 U1 | 11/2012 |
| RU | 138386 U1 | 3/2014 |
| RU | 2600296 C2 | 10/2016 |
| WO | 9501137 A1 | 1/1995 |
| WO | 9748293 A1 | 12/1997 |
| WO | 2004080216 A1 | 9/2004 |
| WO | 2012114322 A1 | 8/2012 |
| WO | 2013138384 A2 | 9/2013 |
| WO | 2013159245 A1 | 10/2013 |
| WO | 2014058678 A1 | 4/2014 |
| WO | WO 2016/020675 | 2/2016 |
| WO | WO 2016/050244 | 4/2016 |
| WO | 2016075747 A1 | 5/2016 |
| WO | 2016194075 A1 | 12/2016 |
| WO | WO 2017/001817 | 1/2017 |

OTHER PUBLICATIONS

Decision to Grant dated Mar. 20, 2018 for Russian Application No. 2017103525, 12 pages.
International Preliminary Report on Patentability for Application No. PCT/GB2018/053187, dated May 22, 2020, 7 pages.
International Preliminary Report on Patentability for Application No. PCT/GB2015/052261, dated Nov. 22, 2016, 14 pages.
International Search Report and Written Opinion for Application No. PCT/GB2015/052261, dated Nov. 5, 2015, 14 pages.
Notice of Reasons for Refusal for Japanese Application No. 2020-524542, dated Feb. 8, 2022, 12 pages.
Notice of Reasons for Rejection for Japanese Application No. 2020-524542, dated Jun. 22, 2021, 12 pages.
Office Action dated Sep. 11, 2018, for Chinese Application No. 201580041869.3, 7 pages.
Office Action for Canadian Application No. 2,955,142, dated Nov. 29, 2017, 4 pages.
Office Action for Canadian Application No. 3082062, dated Jan. 21, 2022, 7 pages.
Office Action for Japanese Application No. 2017-506276, dated Nov. 29, 2017, 4 pages (7 pages with translation).
Office Action For Korean Application No. 10-2020-7013165, dated Dec. 2, 2021, 14 pages.
Office Action dated Sep. 8, 2020 for Russian Patent Application No. 2020114892, 19 pages.
Office Action dated Mar. 21, 2018 for Korean Application No. 10-2017-7003144, 7 pages (13 pages with translation).
Office Action dated Jul. 14, 2021 for Canadian Application No. 3082062, 7 pages.
Search Report for Britain Application No. GB1413835.8, dated Feb. 4, 2015, 4 pages.
Search Report for Japanese Application No. 2020-524542, dated Jun. 14, 2021, 22 pages.

* cited by examiner

VAPOR PROVISION SYSTEMS

PRIORITY CLAIM

The present application is a National Phase entry of PCT Application No. PCT/GB2018/053187, filed Nov. 2, 2018, which claims priority from GB Patent Application No. 1718462.3, filed Nov. 8, 2017, each of which is hereby fully incorporated herein by reference.

FIELD

The present disclosure relates to vapor provision systems such as nicotine delivery systems (e.g. electronic cigarettes and the like).

BACKGROUND

Electronic vapor provision systems such as electronic cigarettes (e-cigarettes) generally contain a vapor precursor material, such as a reservoir of a source liquid containing a formulation, typically including nicotine, or a solid material such as a tobacco-based product, from which a vapor is generated for inhalation by a user, for example through heat vaporization. Thus, a vapor provision system will typically comprise a vapor generation chamber containing a vaporizer, e.g. a heating element, arranged to vaporize a portion of precursor material to generate a vapor in the vapor generation chamber. As a user inhales on the device and electrical power is supplied to the vaporizer, air is drawn into the device through inlet holes and into the vapor generation chamber where the air mixes with the vaporized precursor material and forms a condensation aerosol. There is a flow path between the vapor generation chamber and an opening in the mouthpiece so the incoming air drawn through the vapor generation chamber continues along the flow path to the mouthpiece opening, carrying some of the vapor/condensation aerosol with it, and out through the mouthpiece opening for inhalation by the user. Some electronic cigarettes may also include a flavor element in the flow path through the device to impart additional flavors. Such devices may sometimes be referred to as hybrid devices and the flavor element may, for example, include a portion of tobacco arranged in the air path between the vapor generation chamber and the mouthpiece so that vapor/condensation aerosol drawn through the devices passes through the portion of tobacco before exiting the mouthpiece for user inhalation.

In some systems the supply of power to the vaporizer is activated manually, for example by a user pressing an activation button when they wish to generate vapor for inhalation. Devices that operate in this way may be referred to as button-activated/button-actuated devices. In some other systems the supply of power to the vaporizer is activated automatically in response to user inhalation, for example using a pressure or airflow sensor to detect when a user is inhaling on the device. Devices that operate in this way may be referred to as puff-activated/puff-actuated.

While puff-activated devices are generally considered more convenient for users, there can be some drawbacks with puff-activated devices. For example, puff-activated devices do not start heating the vaporizer until a user is inhaling on the device, which can mean the vaporizer is not running at its optimum temperature during the initial part of a puff, which some users may on some occasions find unsatisfactory. Furthermore, puff-activated devices require a minimum level of inhalation effort to trigger vapor generation (e.g. so that vapor generation is not triggered too easily by ambient changes in pressure), but there may be occasions when some user wishes to inhale vapor with only light inhalation, for example to "graze" on a device while breathing normally. Furthermore still, puff-activated devices typically rely on some form of pressure sensor in fluid communication with the air path through the device, and these puff sensors can be more prone to failure than simple buttons used for button-activated devices, for example because of the potential for condensation to block the air path to the puff sensor or damage the puff sensor itself.

Various approaches are described herein which seek to provide the convenience of puff activation while helping address or mitigate some of the issues discussed above.

SUMMARY

According to a first aspect of certain embodiments there is provided a control unit for a vapor provision system, wherein the control unit comprises: an inhalation sensor; an input button; and control circuitry configured to provide power for the vapor provision system to generate vapor in response to determining from signaling received from the inhalation sensor that a user is inhaling on the vapor provision system and to provide power for the vapor provision system to generate vapor in response to determining from signaling received from the input button that a user has activated the input button for at least a threshold amount of time.

According to another aspect of certain embodiments there is provided a vapor provision system comprising the control unit of the first aspect summarized above.

According to another aspect of certain embodiments there is provided control unit means for vapor provision means, wherein the control unit means comprises: inhalation sensor means; input button means; and control circuitry means configured to provide power for the vapor provision means to generate vapor in response to determining from signaling means received from the inhalation sensor means that a user is inhaling on the vapor provision means and to provide power for the vapor provision means to generate vapor in response to determining from signaling means received from the input button means that a user has activated the input button means for at least a threshold amount of time.

According to another aspect of certain embodiments there is provided a method of operating a control unit for a vapor provision system, wherein the control unit comprises: an inhalation sensor; and an input button; and wherein the method comprises: determining from signaling received from the inhalation sensor if a user is inhaling on the vapor provision system, and if so, providing power for the vapor provision system to generate vapor and determining from signaling received from the input button if a user has activated the input button for at least a threshold amount of time, and if so, providing power for the vapor provision system to generate vapor.

It will be appreciated that features and aspects of the disclosure described above in relation to the first and other aspects of the disclosure are equally applicable to, and may be combined with, embodiments of the disclosure according to other aspects of the disclosure as appropriate, and not just in the specific combinations described above.

BRIEF DESCRIPTION OF THE DRAWINGS

Embodiments of the disclosure will now be described, by way of example only, with reference to the accompanying drawings, in which.

DETAILED DESCRIPTION

Figure 1:
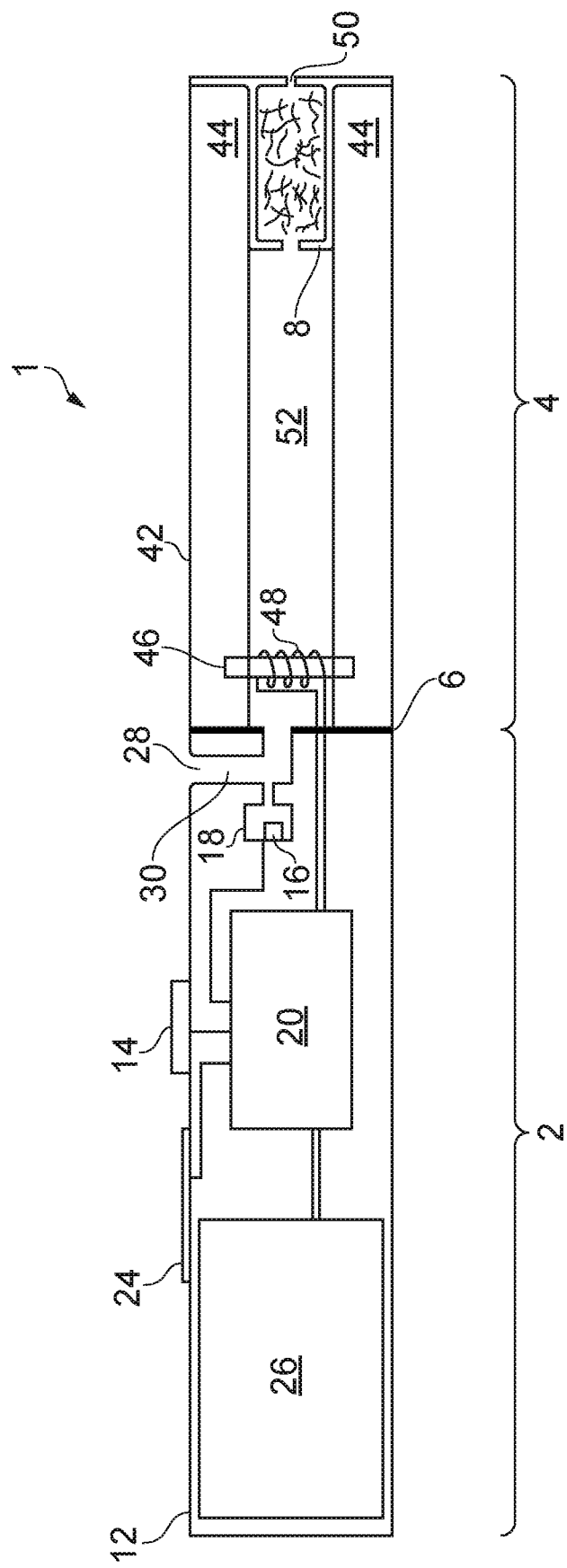
FIG. 1 represents in highly schematic cross-section a vapor provision system in accordance with certain embodiments of the disclosure.

Aspects and features of certain examples and embodiments are discussed/described herein. Some aspects and features of certain examples and embodiments may be implemented conventionally and these are not discussed/described in detail in the interests of brevity. It will thus be appreciated that aspects and features of apparatus and methods discussed herein which are not described in detail may be implemented in accordance with any conventional techniques for implementing such aspects and features.

The present disclosure relates to vapor provision systems, which may also be referred to as aerosol provision systems, such as e-cigarettes, including hybrid devices. Throughout the following description the term "e-cigarette" or "electronic cigarette" may sometimes be used, but it will be appreciated this term may be used interchangeably with vapor provision system/device and electronic vapor provision system/device. Furthermore, and as is common in the technical field, the terms "vapor" and "aerosol", and related terms such as "vaporize", "volatilize" and "aerosolize", may generally be used interchangeably.

Vapor provision systems (e-cigarettes) often, though not always, comprise a modular assembly including both a reusable part and a replaceable (disposable) cartridge part. Often the replaceable cartridge part will comprise the vapor precursor material and the vaporizer and the reusable part will comprise the power supply (e.g. rechargeable battery), activation mechanism (e.g. button or puff sensor), and control circuitry. However, it will be appreciated these different parts may also comprise further elements depending on functionality. For example, for a hybrid device the cartridge part may also comprise the additional flavor element, e.g. a portion of tobacco, provided as an insert ("pod"). In such cases the flavor element insert may itself be removable from the disposable cartridge part so it can be replaced separately from the cartridge, for example to change flavor or because the usable lifetime of the flavor element insert is less than the usable lifetime of the vapor generating components of the cartridge. The reusable device part will often also comprise additional components, such as a user interface for receiving user input and displaying operating status characteristics.

For modular devices a cartridge and control unit are electrically and mechanically coupled together for use, for example using a screw thread, latching or bayonet fixing with appropriately engaging electrical contacts. When the vapor precursor material in a cartridge is exhausted, or the user wishes to switch to a different cartridge having a different vapor precursor material, a cartridge may be removed from the control unit and a replacement cartridge attached in its place. Devices conforming to this type of two-part modular configuration may generally be referred to as two-part devices or multi-part devices.

It is relatively common for electronic cigarettes, including multi-part devices, to have a generally elongate shape and, for the sake of providing a concrete example, certain embodiments of the disclosure described herein will be taken to comprise a generally elongate multi-part device employing disposable cartridges with a tobacco pod insert. However, it will be appreciated the underlying principles described herein may equally be adopted for different electronic cigarette configurations, for example single-part devices or modular devices comprising more than two parts, refillable devices and single-use disposable devices, and non-hybrid devices which do not have an additional flavor element, as well as devices conforming to other overall shapes, for example based on so-called box-mod high performance devices that typically have a more box-like shape. More generally, it will be appreciated certain embodiments of the disclosure are based on electronic cigarettes that are configured to provide activation functionality in accordance with the principles described herein, and the specific constructional aspects of electronic cigarette configured to provide the described activation functionality are not of primary significance.

FIG. 1 is a cross-sectional view through an example e-cigarette 1 in accordance with certain embodiments of the disclosure. The e-cigarette 1 comprises two main components, namely a reusable part 2 and a replaceable/disposable cartridge part 4. In this specific example the e-cigarette 1 is assumed to be a hybrid device with the cartridge part 4 including a removable insert 8 comprising an insert housing containing a portion of shredded tobacco. However, the fact this example is a hybrid device is not in itself directly significant to the device activation functionality as described further herein.

In normal use the reusable part 2 and the cartridge part 4 are releasably coupled together at an interface 6. When the cartridge part is exhausted or the user simply wishes to switch to a different cartridge part, the cartridge part may be removed from the reusable part and a replacement cartridge part attached to the reusable part in its place. The interface 6 provides a structural, electrical and air path connection between the two parts and may be established in accordance with conventional techniques, for example based around a screw thread, latch mechanism, or bayonet fixing with appropriately arranged electrical contacts and openings for establishing the electrical connection and air path between the two parts as appropriate. The specific manner by which the cartridge part 4 mechanically mounts to the reusable part 2 is not significant to the principles described herein, but for the sake of a concrete example is assumed here to comprise a latching mechanism, for example with a portion of the cartridge being received in a corresponding receptacle in the reusable part with cooperating latch engaging elements (not represented in FIG. 1). It will also be appreciated the interface 6 in some implementations may not support an electrical connection between the respective parts. For example, in some implementations a vaporizer may be provided in the reusable part rather than in the cartridge part, or the transfer of electrical power from the reusable part to the cartridge part may be wireless (e.g. based on electromagnetic induction), so that an electrical connection between the reusable part and the cartridge part is not needed.

The cartridge part 4 may in accordance with certain embodiments of the disclosure be broadly conventional. In FIG. 1, the cartridge part 4 comprises a cartridge housing 42 formed of a plastics material. The cartridge housing 42 supports other components of the cartridge part and provides the mechanical interface 6 with the reusable part 2. The cartridge housing is generally circularly symmetric about a longitudinal axis along which the cartridge part couples to the reusable part 2. In this example the cartridge part has a length of around 4 cm and a diameter of around 1.5 cm. However, it will be appreciated the specific geometry, and more generally the overall shapes and materials used, may be different in different implementations.

Within the cartridge housing 42 is a reservoir 44 that contains liquid vapor precursor material. The liquid vapor precursor material may be conventional, and may be referred to as e-liquid. The liquid reservoir 44 in this example has an annular shape with an outer wall defined by the cartridge housing 42 and an inner wall that defines an air path 52 through the cartridge part 4. The reservoir 44 is closed at each end with end walls to contain the e-liquid. The reservoir 44 may be formed in accordance with conventional techniques, for example it may comprise a plastics material and be integrally molded with the cartridge housing 42.

The flavor element insert (tobacco pod) 8 in this example is inserted into an open end of air path 52 opposite to the end of the cartridge 4 which couples to the control unit 2 and is retained by a friction fit. The housing for the flavor element insert 8 includes a collar that abuts the end of the cartridge housing 42 to prevent over insertion. The housing for the flavor element insert 8 also includes an opening at each end to allow air drawn along the air path 52 during use to pass through the flavor element insert 8 and so pick up flavors from the flavorant within (tobacco in this example) before exiting the cartridge 4 though a mouthpiece outlet 50 for user inhalation.

The cartridge part further comprises a wick 46 and a heater (vaporizer) 48 located towards an end of the reservoir 44 opposite to the mouthpiece outlet 50. In this example the wick 46 extends transversely across the cartridge air path 52 with its ends extending into the reservoir 44 of e-liquid through openings in the inner wall of the reservoir 44. The openings in the inner wall of the reservoir are sized to broadly match the dimensions of the wick 46 to provide a reasonable seal against leakage from the liquid reservoir into the cartridge air path without unduly compressing the wick, which may be detrimental to its fluid transfer performance.

The wick 46 and heater 48 are arranged in the cartridge air path 52 such that a region of the cartridge air path 52 around the wick 46 and heater 48 in effect defines a vaporization region for the cartridge part. E-liquid in the reservoir 44 infiltrates the wick 46 through the ends of the wick extending into the reservoir 44 and is drawn along the wick by surface tension/capillary action (i.e. wicking). The heater 48 in this example comprises an electrically resistive wire coiled around the wick 46. In this example the heater 48 comprises a nickel chrome alloy (Cr20Ni80) wire and the wick 46 comprises a glass fiber bundle, but it will be appreciated the specific vaporizer configuration is not significant to the principles described herein. In use electrical power may be supplied to the heater 48 to vaporize an amount of e-liquid (vapor precursor material) drawn to the vicinity of the heater 48 by the wick 46. Vaporized e-liquid may then become entrained in air drawn along the cartridge air path from the vaporization region through the flavor element insert 8 and out the mouthpiece outlet 50 for user inhalation.

The rate at which e-liquid is vaporized by the vaporizer (heater) 48 will depend on the amount (level) of power supplied to the heater 48 during use. Thus electrical power can be applied to the heater to selectively generate vapor from the e-liquid in the cartridge part 4, and furthermore, the rate of vapor generation can be changed by changing the amount of power supplied to the heater 48, for example through pulse width and/or frequency modulation techniques.

The reusable part 2 comprises an outer housing 12 with an opening that defines an air inlet 28 for the e-cigarette, a battery 26 for providing operating power for the electronic cigarette, control circuitry 20 for controlling and monitoring the operation of the electronic cigarette, a user input button 14, an inhalation sensor (puff detector) 16, which in this example comprises a pressure sensor located in a pressure sensor chamber 18, and a visual display 24.

The outer housing 12 may be formed, for example, from a plastics or metallic material and in this example has a circular cross-section generally conforming to the shape and size of the cartridge part 4 so as to provide a smooth transition between the two parts at the interface 6. In this example, the reusable part has a length of around 8 cm so the overall length of the e-cigarette when the cartridge part and reusable part are coupled together is around 12 cm. However, and as already noted, it will be appreciated that the overall shape and scale of an electronic cigarette implementing an embodiment of the disclosure is not significant to the principles described herein.

The air inlet 28 connects to an air path 30 through the reusable part 2. The reusable part air path 30 in turn connects to the cartridge air path 52 across the interface 6 when the reusable part 2 and cartridge part 4 are connected together. The pressure sensor chamber 18 containing the pressure sensor 16 is in fluid communication with the air path 30 in the reusable part 2 (i.e. the pressure sensor chamber 18 branches off from the air path 30 in the reusable part 2). Thus, when a user inhales on the mouthpiece opening 50, there is a drop in pressure in the pressure sensor chamber 18 that may be detected by the pressure sensor 16 and also air is drawn in through the air inlet 28, along the reusable part air path 30, across the interface 6, through the vapor generation region in the vicinity of the atomizer 48 (where vaporized e-liquid becomes entrained in the air flow when the vaporizer is active), along the cartridge air path 52, and out through the mouthpiece opening 50 for user inhalation.

The battery 26 in this example is rechargeable and may be of a conventional type, for example of the kind normally used in electronic cigarettes and other applications requiring provision of relatively high currents over relatively short periods. The battery 26 may be recharged through a charging connector in the reusable part housing 12, for example a USB connector.

The user input button 14 in this example is a conventional mechanical button, for example comprising a spring mounted component which may be pressed by a user to establish an electrical contact. In this regard, the input button may be considered to provide a manual input mechanism for the terminal device, but the specific manner in which the button is implemented is not significant. For example, different forms of mechanical button or touch-sensitive button (e.g. based on capacitive or optical sensing techniques) may be used in other implementations. The specific manner in which the button is implemented may, for example, be selected having regard to a desired aesthetic appearance.

The display 24 is provided to give a user with a visual indication of various characteristics associated with the electronic cigarette, for example current power setting information, remaining battery power, and so forth. The display may be implemented in various ways. In this example the display 24 comprises a conventional pixilated LCD screen that may be driven to display the desired information in accordance with conventional techniques. In other implementations the display may comprise one or more discrete indicators, for example LEDs, that are arranged to display the desired information, for example through particular colors and/or flash sequences. More generally, the manner in which the display is provided and information is displayed to a user using the display is not significant to the principles described herein. Some embodiments may not include a visual display and may include other means for providing a user with information relating to operating characteristics of the electronic cigarette, for example using audio signaling or haptic feedback, or may not include any means for providing a user with information relating to operating characteristics of the electronic cigarette.

The control circuitry 20 is suitably configured/programmed to control the operation of the electronic cigarette to provide functionality in accordance with embodiments of the disclosure as described further herein, as well as for providing conventional operating functions of the electronic cigarette in line with the established techniques for controlling such devices. The control circuitry (processor circuitry) 20 may be considered to logically comprise various sub-units/circuitry elements associated with different aspects of the electronic cigarette's operation in accordance with the principles described herein and other conventional operating aspects of electronic cigarettes, such as display driving circuitry and user input detection. It will be appreciated the functionality of the control circuitry 20 can be provided in various different ways, for example using one or more suitably programmed programmable computer(s) and/or one or more suitably configured application-specific integrated circuit(s)/circuitry/chip(s)/chipset(s) configured to provide the desired functionality.

Thus the vapor provision system 1 comprises a user input button 14 and an inhalation sensor 16. In accordance with certain embodiments of the disclosure the control circuitry 20 is configured to receive signaling from the inhalation sensor 16 and to use this signaling to determine if a user is inhaling in the electronic cigarette and also to receive signaling from the input button 14 and to use this signaling to determine if a user is pressing (i.e. activating) the input button. These aspects of the operation of the electronic cigarette (i.e. puff detection and button press detection) may in themselves be performed in accordance with established techniques (for example using conventional inhalation sensor and inhalation sensor signal processing techniques and using conventional input button and input button signal processing techniques). However, the control circuitry 20 in accordance with certain embodiments of the disclosure is configured to control the supply of power to the vaporizer (i.e. to activate vapor generation) in response to determining either one of a user inhaling on the electronic cigarette or a user pressing the input button for at least a predetermined threshold time, for example 0.3 seconds. Thus, in accordance with certain embodiments of the disclosure, the electronic cigarette of FIG. 1 allows for both puff activation and button activation. This means a user may take advantage of the convenience of a puff activation, but may also use choose to, in effect, override this by using the button for manual activation, for example to avoid a delay in the vaporizer reaching an optimum temperature when the user starts inhaling, or to generate vapor without inhaling sufficiently deeply to trigger puff detection. What is more, providing the facility for both puff activation and button activation in the same device provides redundancy against one or other activation mechanism failing. For example, if the puff sensor fails, the device can still be used with button activation, and if the input button fails, the device can still be used with puff-activation.

Furthermore, as noted above in accordance with certain embodiments of the disclosure the control circuitry may be configured to activate vapor generation in response to a user pressing the button for at least a minimum threshold period of time, or example 0.3 seconds. Embodiments in accordance with this approach mean the input button 14 may also be used to receive user input for means other than activating vapor generation when a user activates the button for less than 0.3 seconds. Thus, in some implementations the control circuitry may respond to activation of the input button 14 that does not meet the threshold duration for triggering vapor generation in a different way, for example to allow a user to configure an aspect of the electronic cigarette, such as a power setting, or to trigger the electronic cigarette to provide an indication of remaining battery power. In this regard the functionality of the user input button when activated for less than the threshold duration for triggering vapor generation may be in accordance with any conventional approach for user interaction with an electronic cigarette using a button for purposes other than activating vapor generation. In this regard the inventors have found that a predetermined threshold time of 0.3 seconds can in some cases provide an appropriate threshold to help distinguish between a user activating the button to trigger vapor generation (i.e. activating the button for at least 0.3 seconds) and a user activating the button for another reason (i.e. activating the band for less than 0.3 seconds) without unduly delaying vapor generation when a user does wish to use the button for this purpose. However, it will be appreciated different threshold time periods may be used in accordance with different implementations, and furthermore, in some examples this may be user configurable. In some implementations the threshold amount of time may be an amount of time selected which is at least: 0.2 seconds; e.g., at least 0.25 seconds; e.g., at least 0.3 seconds; e.g., at least 0.35 seconds; e.g., at least 0.4 seconds; e.g., at least 0.45 seconds; e.g., at least 0.5 seconds; e.g., at least 0.55 seconds; e.g., at least 0.6 seconds; e.g., at least 0.65 seconds; e.g., at least 0.7 seconds; e.g., at least 0.75 seconds; e.g., at least 0.8 seconds; e.g., at least 0.85 seconds; e.g., at least 0.9 seconds; e.g., at least 0.95 seconds; e.g., at least 1 second, or more.

Figure 2:
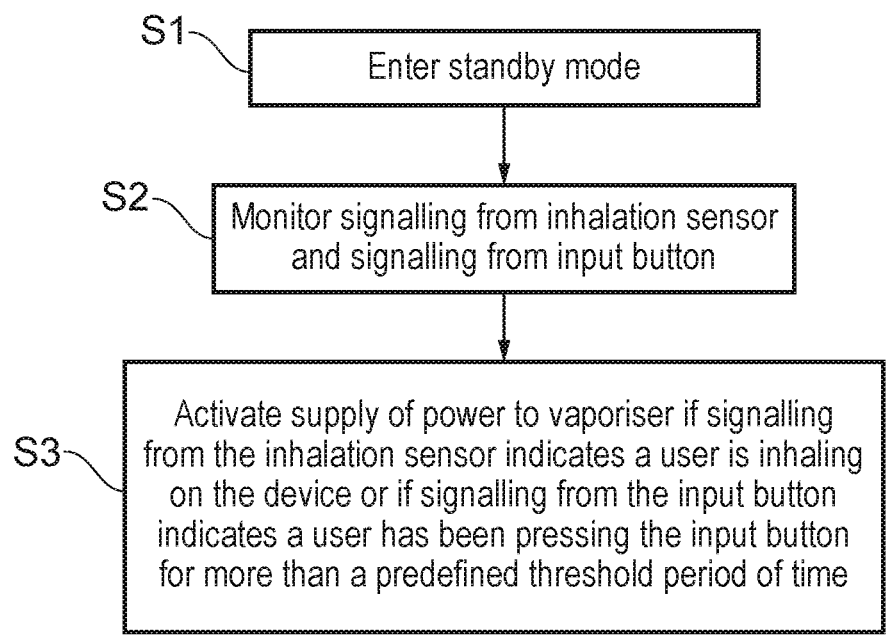
FIG. 2 is a flow diagram representing some operating steps for the vapor provision system of FIG. 1 in accordance with certain embodiments of the disclosure.

FIG. 2 is a flow diagram schematically representing some operating aspects of the vapor provision system of FIG. 1 in accordance with certain embodiments of the disclosure.

In S1 the vapor provision system 1 enters a standby state. As is common for electronic cigarettes, the vapor provision system 1 supports three basic operating states, namely an "off" state, an "on" state, and a "standby" state.

In the off state, the electronic cigarette is unable to generate vapor (i.e. the power supply control circuitry is prevented from supplying power to the vaporizer/heater in the off state). The electronic cigarette may, for example, be placed in the off state between use sessions, for example when the electronic cigarette might be set aside or placed in a user's pocket or bag.

In the on (or active) state, the electronic cigarette is actively generating vapor (i.e. the power supply control circuitry is providing power to the vaporizer/heater). The electronic cigarette will thus typically be in the on state when a user is in the process of inhaling vapor from the electronic cigarette.

In the standby state the electronic cigarette is ready to generate vapor (i.e. ready to apply power to the vaporizer) in response to user activation, but is not currently doing so. The electronic cigarette will typically be in the standby state when a user initially exits the off state to begin a session of use (i.e. when a user initially turned on the electronic cigarette), or between uses during an ongoing session of use (i.e. between puffs when the user using the electronic cigarette). As noted above, in accordance with certain embodiments of the disclosure, the electronic cigarette is configured to generate vapor in response to at least two different forms of user activation namely the user inhaling on the device (detected by the inhalation sensor 16) and the user pressing the input button for at least a threshold amount of time. For the sake of providing a concrete example, it is assumed here the electronic cigarette enters the standby state in S1 by virtue of the user bringing the device out of the off state to begin a session of use. However, the processing represented in FIG. 2 is in this example the same regardless of whether the electronic cigarette enters the standby mode in S1 from being first switched on to begin a session of use or between puffs during an ongoing session of use. The manner in which the electronic cigarette is caused to switch from the off state to the standby state will be a matter of implementation and is not significant here. For example, to transition from the off state to the standby state the user may be required to press the input button 14 in a particular sequence, for example multiple presses within a predetermined time.

As represented in S2 in FIG. 2, while in the standby mode the control circuitry is configured to monitor signaling from the inhalation sensor 16 and from the input button 14. In particular, the control circuitry is configured to monitor for signaling from the inhalation sensor 16 which indicates a user is inhaling on the electronic cigarette and to monitor for signaling from the input button 14 which indicates a user is pressing the input button. The specific manner in which this monitoring is performed will depend on the specific circuitry implementation. For example, in some example implementations the control circuitry may be configured to determine the status of the inhalation sensor and/or input button from output signaling received from these components according to a regular sampling schedule, for example every 10 ms. However, in other example implementations the control circuitry might not regularly poll the output signaling from the inhalation sensor and/or input button according to a sampling schedule, but may instead rely on interrupt signaling received from the inhalation sensor and/or button to indicate when each is activated. In this regard, it will be appreciated the specific manner in which the monitoring is undertaken is not significant to the principles described herein.

As indicated in S3, the control circuitry determines when either (i) signaling from the inhalation sensor indicates a user is inhaling the device; or (ii) signaling from the input button indicates a user has pressed input button for more than the predefined threshold period of time (e.g. 0.3 seconds in this example). If either one of these trigger conditions is determined to be met, the control circuitry responds by providing power to the vaporizer to generate vapor. In this regard it will be appreciated the control circuitry providing power typically involves the control circuitry activating a switch, for example a MOSFET switch, to connect the power supply 26 to electrical contacts at the interface 6 between the control unit to and the cartridge 4. Thus, when a cartridge is connected to the control unit 2, the power provided by the control circuitry in response to determining one (or both) of the two trigger criteria are met results in activation of the vaporizer and corresponding vapor generation for user inhalation.

Thus, as discussed above, approaches in accordance with embodiments of the disclosure provide a user with multiple different mechanisms for activating vapor generation, and furthermore do so in a way which allows an input button to be used for vapor generation in addition to being used for other means (i.e. when pressed for less than the predefined threshold amount of time).

In accordance with certain embodiments of the disclosure, when vapor generation is triggered in S3 in response to determining a user is inhaling on the electronic cigarette, the control circuitry may be configured to stop providing power to the vaporizer for vapor generation when it is determined from signaling received from the inhalation sensor that the user has stopped inhaling on the electronic cigarette. Similarly, when vapor generation is triggered in S3 in response to determining a user has pressed the input button for at least the threshold amount of time, the control circuitry may be configured to stop providing power to the vaporizer for vapor generation when it is determined from signaling received from the input button that the user has stopped pressing the input button.

In some implementations, when vapor generation is triggered in S3 by one of the trigger conditions being met, vapor generation may continue (i.e. the control circuitry may be configured to continue to provide power for the vaporizer) if the other trigger condition is deemed to be met, even after the initial trigger condition stops being met. For example, in such an implementation a user may trigger vapor generation by activating the input button by more than the threshold amount of time, and then midway through a puff may release the input button, but so long as an inhalation sensor continues to detect the puff is ongoing, the control circuitry may continue providing power to the vaporizer. However, in other implementations when vapor generation is triggered by one of the trigger conditions being met, vapor generation may cease when this trigger condition is no longer met, regardless of whether the other trigger condition is met. For example, in such an implementation a user may trigger vapor generation by activating the input button by more than the threshold amount of time, and then may subsequently release the input button, and this may cause the control circuitry to stop providing power to the vaporizer even if the user continues to inhale on the electronic cigarette. That is to say, in accordance with certain implementations, the control circuitry may be configured to in effect disregard signaling received from the inhalation sensor and/or disable an operating aspect of the inhalation sensor when providing power for the vaporizer in response to determining from signaling received from the input button that the user has activated the input button for at least the threshold amount of time.

In some implementations, the control circuitry may be configured to stop providing power to the vaporizer after a predetermined period of time of continuously supplying power to the vaporizer, i.e. after what might be referred to as a maximum allowed continuous activation time, regardless of whether the inhalation sensor indicates the user is inhaling on the electronic cigarette or whether the input button indicates the user is still pressing the input button. This may provide what is in effect a safety cut off, for example in case of failure in either the inhalation sensor or input button which results in one of them indicating continuous activation (e.g. because the input button has become stuck in the activated position). The maximum allowed continuous activation time may, for example be between 6 seconds and 10 seconds; e.g., between 6.5 seconds and 9.5 seconds; e.g., between 7 seconds and 9 seconds; e.g., between 7.5 seconds and 8.5 seconds.

As noted above, in accordance with some example implementations the control unit may comprise a rechargeable battery for supplying power for the vaporizer under the control of the control circuitry in accordance with the principles described herein, and in some examples the control circuitry may be configured to provide power for the vaporizer in response to determining user activation using wither the inhalation sensor or the push button when the control unit is coupled to an external power supply to charge the rechargeable battery, as well as when the batter is not being charged.

While the above-described embodiments have in some respects focused on some specific example vapor provision systems, it will be appreciated the same principles can be applied for vapor provision systems using other technologies. That is to say, the specific manner in which various aspects of the vapor provision system function are not directly relevant to the principles underlying the examples described herein.

For example, whereas the above-described embodiments have primarily focused on devices having an electrical heater based vaporizer for heating a liquid vapor precursor material, the same principles may be adopted in accordance with vaporizers based on other technologies, for example piezoelectric vibrator based vaporizers or optical heating vaporizers, and also devices based on other aerosol precursor materials, for example solid materials, such as plant derived materials, such as tobacco derivative materials, or other forms of vapor precursor materials, such as gel, paste or foam based vapor precursor materials.

Furthermore, and as already noted, it will be appreciated the above-described approaches for providing multiple independent activation mechanisms for vapor generation in an electronic cigarette may be implemented in cigarettes having a different overall construction that represented in FIG. 1. For example, the same principles may be adopted in an electronic cigarette which does not comprise a two-part modular construction, but which instead comprises a single-part device, for example a disposable (i.e. non-rechargeable and non-refillable) device. Furthermore, in some implementations of a modular device, the arrangement of components may be different. For example, in some implementations the control unit may also comprise the vaporizer with a replaceable cartridge providing a source of vapor precursor material for the vaporizer to use to generate vapor. Furthermore still, whereas in the above-described examples the electronic cigarette 1 includes a flavor insert 8, other examples implementations may not include such an additional flavor element.

Thus there has been described a vapor provision system comprising: an inhalation sensor; an input button; control circuitry and a vaporizer for generating vapor from a vapor precursor material when provided with power from the control circuitry, wherein the control circuitry configured to provide power for the vaporizer to generate vapor both in response to determining from signaling received from the inhalation sensor that a user is inhaling on the vapor provision system and in response to determining from signaling received from the input button that a user has activated the input button for at least a threshold amount of time.

In order to address various issues and advance the art, this disclosure shows by way of illustration various embodiments in which the claimed invention(s) may be practiced. The advantages and features of the disclosure are of a representative sample of embodiments only, and are not exhaustive and/or exclusive. They are presented only to assist in understanding and to teach the claimed invention(s). It is to be understood that advantages, embodiments, examples, functions, features, structures, and/or other aspects of the disclosure are not to be considered limitations on the disclosure as defined by the claims or limitations on equivalents to the claims, and that other embodiments may be utilized and modifications may be made without departing from the scope of the claims. Various embodiments may suitably comprise, consist of, or consist essentially of, various combinations of the disclosed elements, components, features, parts, steps, means, etc. other than those specifically described herein, and it will thus be appreciated that features of the dependent claims may be combined with features of the independent claims in combinations other than those explicitly set out in the claims. The disclosure may include other inventions not presently claimed, but which may be claimed in future.

The invention claimed is:

1. A control unit for a vapor provision system, the control unit comprising:
   an inhalation sensor;
   an input button; and
   control circuitry configured to provide power for the vapor provision system to generate vapor in response to either of:
   determining from signaling received from the inhalation sensor that a user is inhaling on the vapor provision system,
   determining from signaling received from the input button that the user has activated the input button for at least a threshold amount of time;
   wherein the control circuitry is configured to do at least one of disregard signaling received from the inhalation sensor or disable an operating aspect of the inhalation sensor when providing power for the vapor provision system to generate vapor in response to determining from signaling received from the input button that the user has activated the input button for at least the threshold amount of time; and
   wherein the control circuitry is configured when providing power for the vapor provision system to generate vapor in response to determining the user is inhaling on the vapor provision system to stop providing power for the vapor provision system to generate vapor in response to determining from signaling received from the inhalation sensor that the user has stopped inhaling on the vapor provision system.

2. The control unit of claim 1, wherein the threshold amount of time is an amount of time selected from the group consisting of: at least 0.2 seconds; at least 0.25 seconds; at least 0.3 seconds; at least 0.35 seconds; at least 0.4 seconds; at least 0.45 seconds; at least 0.5 seconds; at least 0.55 seconds; at least 0.6 seconds; at least 0.65 seconds; at least 0.7 seconds; at least 0.75 seconds; at least 0.8 seconds; at least 0.85 seconds; at least 0.9 seconds; at least 0.95 seconds; and at least 1 second.

3. The control unit of claim 1, wherein the control circuitry is configured to stop providing power for the vapor provision system to generate vapor after providing power for the vapor provision system to generate vapor for a maximum allowed continuous activation time.

4. The control unit of claim 3, wherein the maximum allowed continuous activation time is in a range selected from the group consisting of: between 6 seconds and 10 seconds; between 6.5 seconds and 9.5 seconds; between 7 seconds and 9 seconds; and between 7.5 seconds and 8.5 seconds.

5. The control unit of claim 1, further comprising a rechargeable battery as a source of power for the vapor provision system to generate vapor, and wherein the control circuitry is still able to provide power for the vapor provision system to generate vapor when the control unit is coupled to an external power supply to charge the rechargeable battery.

6. The control unit of claim 1, further comprising a vaporizer for generating vapor when provided with power by the control circuitry.

7. A vapor provision system comprising the control unit of claim 1, a vaporizer for generating vapor when provided with power by the control circuitry, and a replaceable cartridge part comprising a vapor precursor material from which the vaporizer generates vapor when provided with power from the control circuitry.

8. The vapor provision system of claim 7, wherein the cartridge part further includes the vaporizer.

9. The vapor provision system of claim 7, further comprising a flavor imparting element arranged between the vaporizer and a vapor outlet for the vapor provision system, or between an air inlet for the vapor provision system and the vaporizer, to impart a flavor to vapor generated by the vaporizer during use.

10. The vapor provision system of 9 wherein the flavor imparting element comprises a portion of tobacco.

11. Control unit means for vapor provision means, the control unit means comprising:
    inhalation sensor means;
    input button means; and
    control circuitry means configured to provide power for the vapor provision means to generate vapor in response to either of:
    determining from signaling means received from the inhalation sensor means that a user is inhaling on the vapor provision means, and
    determining from signaling means received from the input button means that the user has activated the input button means for at least a threshold amount of time; and
    configuring the control circuitry to do at least one of disregard signaling received from the inhalation sensor or disable an operating aspect of the inhalation sensor when providing power for the vapor provision system to generate vapor in response to determining from signaling received from the input button that the user has activated the input button for at least the threshold amount of time, and
    configuring the control circuitry in response to providing power for the vapor provision system to generate vapor in response to determining the user is inhaling on the vapor provision system to stop providing power for the vapor provision system to generate vapor in response to determining from signaling received from the inhalation sensor that the user has stopped inhaling on the vapor provision system.

12. A method of operating a control unit for a vapor provision system, wherein the control unit comprises an inhalation sensor, and an input button, the method comprising:
    determining from signaling received from the inhalation sensor if a user is inhaling on the vapor provision system, and if so, providing power for the vapor provision system to generate vapor;
    determining from signaling received from the input button if a user has activated the input button for at least a threshold amount of time, and if so, providing power for the vapor provision system to generate vapor, and
    configuring the control circuitry in response to providing power for the vapor provision system to generate vapor in response to determining the user is inhaling on the vapor provision system to stop providing power for the vapor provision system to generate vapor in response to determining from signaling received from the inhalation sensor that the user has stopped inhaling on the vapor provision system.

13. A control unit for a vapor provision system, the control unit comprising:
    an inhalation sensor;
    an input button; and
    control circuitry configured to provide power for the vapor provision system to generate vapor in response to either of:
    determining from signaling received from the inhalation sensor that a user is inhaling on the vapor provision system,
    determining from signaling received from the input button that the user has activated the input button for at least a threshold amount of time;
    wherein the control circuitry is configured to do at least one of disregard signaling received from the inhalation sensor or disable an operating aspect of the inhalation sensor when providing power for the vapor provision system to generate vapor in response to determining from signaling received from the input button that the user has activated the input button for at least the threshold amount of time; and
    wherein the control circuitry is configured when providing power for the vapor provision system to generate vapor in response to determining the user had activated the input button for at least a threshold amount of time to stop providing power for the vapor provision system to generate vapor in response to determining from signaling received from the inhalation sensor that the user has stopped activating the input button.

* * * * *